(12) United States Patent
Lazic

(10) Patent No.: US 12,115,299 B2
(45) Date of Patent: Oct. 15, 2024

(54) FLUSHING AND ASPIRATING DEVICE

(71) Applicant: Lazic Besitz GmbH & Co. KG, Tuttlingen (DE)

(72) Inventor: Daniel Lazic, Tuttlingen (DE)

(73) Assignee: Lazic Besitz GmbH & Co. KG, Tuttlingen (DE)

( * ) Notice: Subject to any disclaimer, the term of this patent is extended or adjusted under 35 U.S.C. 154(b) by 926 days.

(21) Appl. No.: 16/392,907

(22) Filed: Apr. 24, 2019

(65) Prior Publication Data

US 2019/0328942 A1  Oct. 31, 2019

(30) Foreign Application Priority Data

Apr. 25, 2018 (EP) .................................... 18169257

(51) Int. Cl.
*A61M 1/00* (2006.01)
(52) U.S. Cl.
CPC .......... *A61M 1/7413* (2021.05); *A61M 1/743* (2021.05); *A61M 1/774* (2021.05)
(58) Field of Classification Search
CPC .... A61M 1/0062; A61M 1/743; A61M 1/774; A61M 1/7413
See application file for complete search history.

(56) References Cited

U.S. PATENT DOCUMENTS

| | | | | |
|---|---|---|---|---|
| 3,131,722 A | * | 5/1964 | Abbott | F16K 11/07 137/625.69 |
| 4,217,934 A | * | 8/1980 | Peters | F16K 17/02 137/625.69 |
| 4,502,508 A | * | 3/1985 | Lester | F16K 11/0712 137/625.48 |
| 4,907,744 A | * | 3/1990 | Jousson | A61C 17/0202 137/625.48 |
| 5,449,145 A | | 9/1995 | Wortrich | |
| 5,658,249 A | | 8/1997 | Beland et al. | |
| 7,779,842 B1 | * | 8/2010 | Russo | A61M 1/743 128/207.14 |
| 2009/0187146 A1 | | 7/2009 | Landman et al. | |
| 2017/0368239 A1 | * | 12/2017 | Askem | A61M 1/90 |

FOREIGN PATENT DOCUMENTS

| | | |
|---|---|---|
| DE | 3309917 C2 | 10/1983 |
| DE | 33 09 916 A1 | 3/1984 |
| DE | 20 2014 000 600 U1 | 5/2014 |
| GB | 2215210 A * | 9/1989 ......... A61B 1/00068 |

* cited by examiner

*Primary Examiner* — Lauren P Farrar
(74) *Attorney, Agent, or Firm* — Orbit IP, LLP

(57) ABSTRACT

A flushing and aspirating device includes a device housing with an aspirating channel, a flushing channel, a flushing and aspirating channel and a valve chamber in which the channels empty or emerge therefrom, respectively. A manually operable valve push button is movably guided in the valve chamber against the force of a reset spring and which has at least one sealing section for controlling the connection of the flushing and aspirating channel to the aspirating channel and/or the flushing channel. The valve push button including the at least one sealing section is formed as a single piece of an elastic rubber material, such as silicone.

5 Claims, 6 Drawing Sheets

FLUSHING AND ASPIRATING DEVICE

CROSS-REFERENCE TO RELATED APPLICATIONS

This application claims priority to European Patent Application EP 18 169 257.5 filed Apr. 25, 2018, the entire contents of which are hereby incorporated in full by this reference.

DESCRIPTION

Field of the Invention

The invention relates to a flushing and aspirating device, comprising a device housing with an aspirating channel, a flushing channel and a flushing and aspirating channel and with a valve chamber in which the channels empty or emerge therefrom, respectively, and comprising a manually operable valve push button which is movably guided in the valve chamber against the force of a reset spring and which has at least one sealing section for controlling the connection of the flushing and aspirating channel to the aspirating channel and/or the flushing channel.

Background of the Invention

Such a flushing and aspirating device is known for example from DE 33 09 916 C2, DE 33 09 917 C2 or DE 33 09 916 C2.

Such flushing and aspirating devices are used, for example, for medical purposes, such as for the cleaning of wounds in surgery operations. During an operation, either fluid is to be aspirated herein or flushing liquid is to be supplied. By means of a valve, the flushing liquid and the aspiration capacity are switched on and off respectively. Such a flushing and aspirating device is to be cheap and made of a plastic material, since it is disposed of after a single use.

In the flushing and aspirating device known from DE 33 09 916 C2, DE 33 09 917 C2 or DE 33 09 916 C2, the valve push button is made from a stiff plastic and it has three elastic sealing rings made from an elastomer material mounted on it, being in contact with the wall of the valve chamber. The reset spring is braced on the one hand against the bottom of the valve chamber and on the other hand against the underside of the valve push button.

Accordingly, the problem which the present invention proposes to solve is to reduce the number of individual parts in a flushing and aspirating device of the kind mentioned above and to thereby simplify the assembly and to lower the manufacturing costs.

SUMMARY OF THE INVENTION

This problem is solved according to the invention in that the valve push button including the at least one sealing section is formed as a single piece of an elastic rubber material, especially of silicone (e.g., silicone rubber or silicone elastomers).

In an especially preferred embodiment, the valve push button comprises a bore, which is open towards the housing bottom of the valve chamber, with a shoulder, especially a base of the bore, against which the reset spring is braced.

In another embodiment, a guiding projection rises up from a housing bottom of the valve chamber, on which both the valve push button and the reset spring are guided. In this case, the valve push button may comprise a stepped blind bore, which is open towards the housing bottom of the valve chamber, having a smaller and a larger bore diameter and having a shoulder, especially an annular shoulder, against which the reset spring is braced, the smaller bore diameter corresponding to the diameter of the guiding projection and the larger bore diameter corresponding at least to the outer diameter of the reset spring.

In both embodiments, for reasons of stability it is advantageous for the shoulder to be situated in a broad middle or actuating section of the valve push button, so that the valve push button is deformed as little as possible at its sealing end.

The valve push button preferably comprises an actuating section protruding from the device housing, a cylindrical shaft and a cylindrical middle section in between, relative to which the actuating section and the shaft are respectively set back radially inwards. For example, on the shaft, a sealing section is formed as a single piece, in the form of a radially outwardly protruding annular sealing lip, which blocks the connection of the the flushing and aspirating channel to the flushing channel in a first valve position of the valve push button and releases it in a second valve position of the valve push button. For example, on the middle section, a sealing section is formed as a single piece, in the form of a radially outwardly protruding annular sealing lip, which releases the connection of the flushing and aspirating channel to the aspirating channel in the first valve position of the valve push button and blocks it in the second valve position.

Preferably, the valve chamber is configured stepped, with a first valve chamber having a larger diameter, in which the aspirating channel and the flushing and aspirating channel empty or emerge therefrom, and with a second valve chamber having a smaller diameter, in which the flushing channel empties. The diameter of the shaft is preferably smaller than the diameter of the second valve chamber, and the sealing section formed on the shaft in the first valve position of the valve push button is situated at the side facing the first valve chamber of the flushing channel emptying the second valve chamber and in the second valve position it is situated at the side facing away from the first valve chamber of the flushing channel emptying into the second valve chamber.

Especially preferably, the aspirating channel comprises an outwardly open aspiration regulating opening, which is situated advantageously on the same side of the housing as the valve push button. The aspiration regulating opening is opened to varying width by the operator, depending on the desired aspiration capacity.

Further advantages of the invention will emerge from the description, the claims, and the drawing. Likewise, the features mentioned above and those indicated below may each find use individually or in any desired combinations of them. The embodiments indicated and described should not be taken as a definite listing, but instead have an exemplary nature for the description of the invention.

DETAILED DESCRIPTION OF THE PREFERRED EMBODIMENTS

Figure 1A:
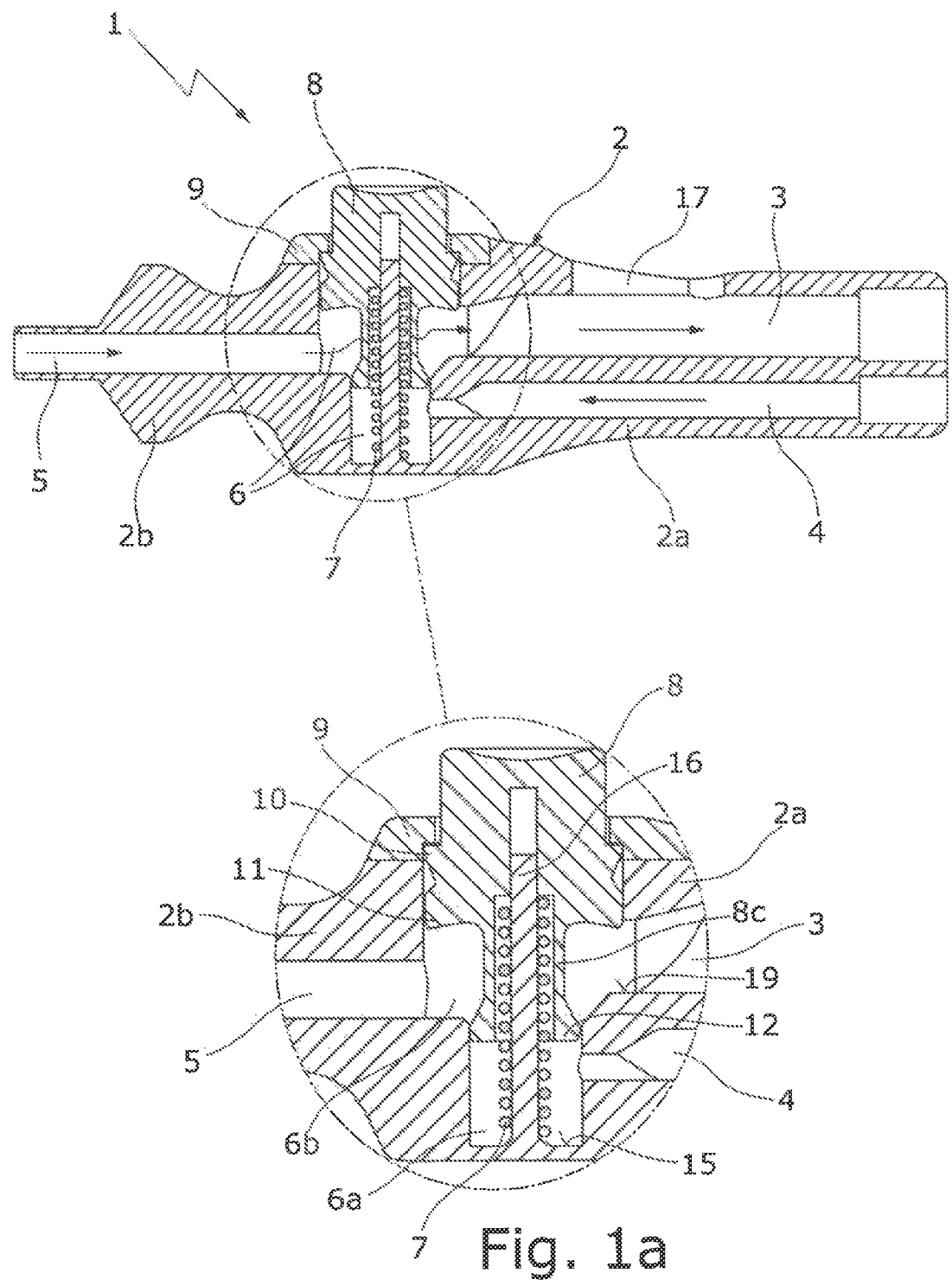
FIGS. 1a, 1b show a longitudinal section of a first embodiment of the flushing and aspirating device according to the invention with a valve push button, which is shown in FIG. 1a in a valve starting position and in FIG. 1b in a valve end position.
Figure 1B:
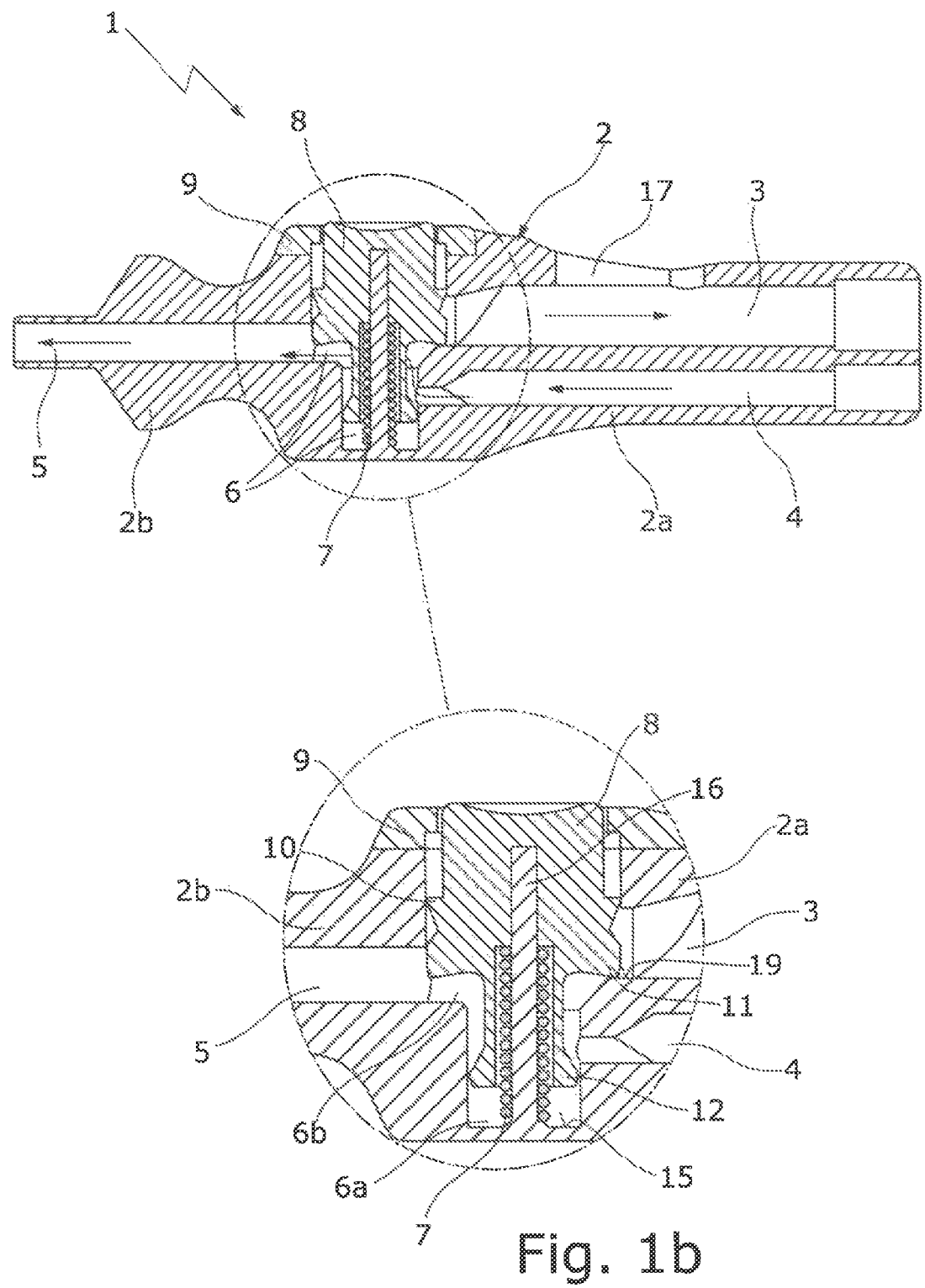

The flushing and aspirating device 1 shown in FIGS. 1a, 1b serves for either aspirating fluid or supplying flushing liquid during a medical operation.

The flushing and aspirating device 1 comprises a single-piece plastic injection moulded device housing 2 with an aspirating channel 3, a flushing channel 4 and a flushing and aspirating channel 5 and with a valve chamber 6 in which the channels 3-5 empty or emerge therefrom, respectively, and comprises a manually operable valve push button 8 which is movably guided in the valve chamber 6 against the force of a helical reset spring (compression spring) 7, which controls the connection of the flushing and aspirating channel 5 to the aspirating channel 3 and/or the flushing channel 4.

The device housing 2 is divided by the valve chamber 6 into a distal housing end 2a, in which the aspirating channel 3 and the flushing channel 4 run parallel to each other, and a proximal housing end 2b, in which the flushing and aspirating channel 5 runs. The valve chamber 6 is formed by a stepped bore open at one end (the top in FIGS. 1a, 1b), having a lower valve chamber 6a with a smaller diameter and an upper valve chamber 6b with a larger diameter. In each case on the right side of the valve chamber 6, the aspirating channel 3 emerges from the upper valve chamber 6b and the flushing channel 4 empties into the lower valve chamber 6a. Between the aspirating channel and the flushing channel 3, 4, but on the left side of the valve chamber 6, the flushing and aspirating channel 5 empties into the upper valve chamber 6b. The valve push button 8 formed as a single piece of silicone (such as silicone rubber or silicone elastomer) is inserted from above into the valve chamber 6 and secured therein by means of an annular plastic cover 9, which after the assembly of the valve push button 8 and the reset spring 7 is joined to the device housing 2, especially by ultrasound welding.

Figure 2A:
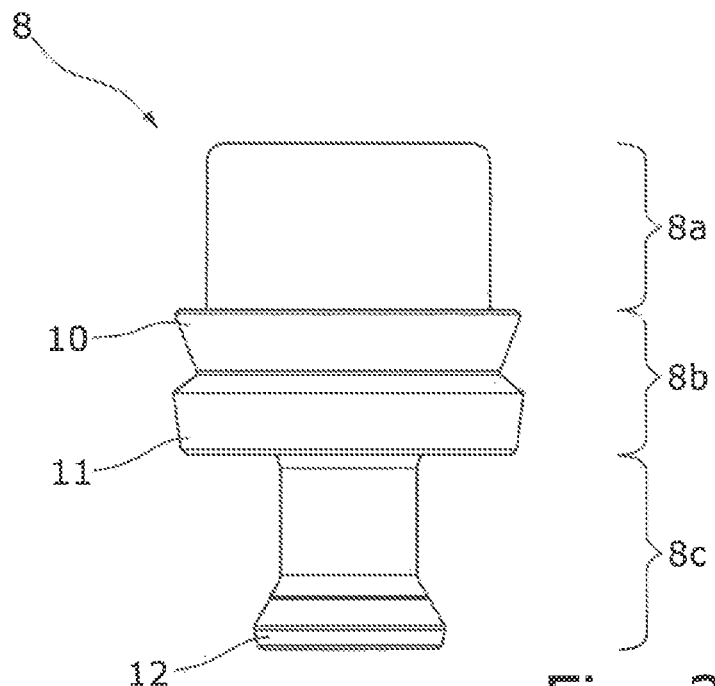
FIGS. 2a, 2b show a side view (FIG. 2a) and a cross sectional view (FIG. 2b) of the valve push button shown in FIGS. 1a, 1b.
Figure 2B:
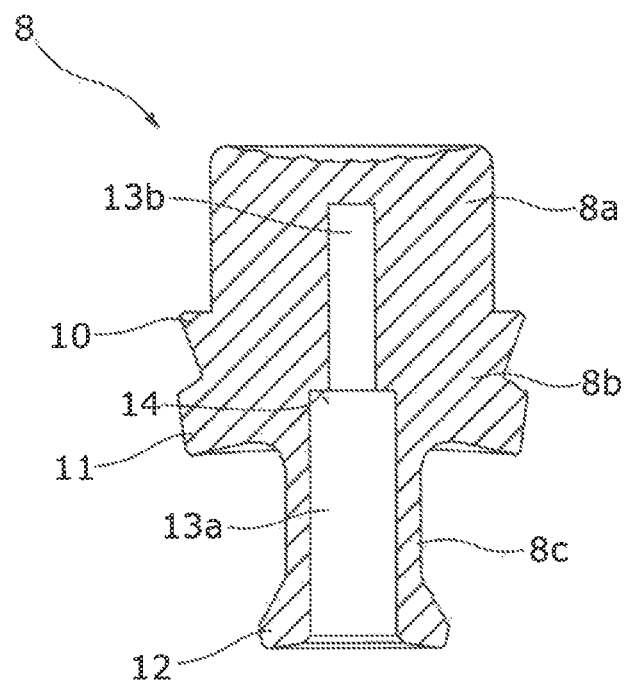

As shown in FIGS. 2a, 2b, the valve push button 8 has on top a cylindrical actuating section 8a, a cylindrical middle section 8b with two radially outwardly projecting annular sealing lips 10, 11 and at the bottom a cylindrical shaft 8c with a radially outwardly projecting annular sealing lip 12. The three sealing lips 10, 11, 12 are formed as a single piece on the valve push button 8. The outside of the sealing lip 12 extends slightly conically downwards. The outer diameter of the sealing lips 10, 11 formed on the middle section 8b is larger than the outer diameter of the actuating section 8a, which in turn is larger than the outer diameter of the sealing lip 12 formed on the shaft 8c. In the valve push button 8 there runs a stepped blind bore, which is open at the bottom and has a lower bore section 13a with larger bore diameter, an upper bore section 13b with a smaller bore diameter, and between them an annular shoulder 14 in the middle section 8b.

A cylindrical guiding projection 16 rises up from the housing bottom 15 of the valve chamber 6, on which both the reset spring 7 and the valve push button 8 are movably guided. For this, the smaller bore diameter of the upper bore section 13b corresponds to the diameter of the guiding projection 16 and the larger bore diameter of the lower bore section 13a corresponds to the outer diameter of the reset spring 7. The reset spring 7 is braced at one end against the housing bottom 15 and at the other end against the annular shoulder 14 of the valve push button 8. Thanks to the cylindrical or rotationally symmetrical form of the valve push button 8, the force can be optimally divided by the actuation and by the reset spring 7. Furthermore, no direction of turning during installation needs to be heeded when installing the valve push button 8.

The reset spring 7 biases the valve push button 8 upwards into the valve starting position shown in FIG. 1a, in which the sealing edge 10 formed on the middle section 8b rests against the cover 9.

In the valve starting position, the connection of the flushing and aspirating channel 5 to the aspirating channel 3 is opened up by the annular chamber, formed by the shaft 8c which is set back radially inwardly, and the connection of the flushing channel 4 to the flushing and aspirating channel 5 is blocked by the sealing lip 12 formed at the bottom on the shaft 8c, which blocks off the lower valve chamber 6a from the upper valve chamber 6b above the flushing channel 4. The diameter of the shaft should be as small as possible so that the annular chamber is as large as possible and therefore presents no obstacle which might possibly result in clogging. The flushing water under pressure in the lower valve chamber 6a on the one hand presses from below against the sealing lip 12, which is thereby curved upwards elastically until its originally conical exterior is now pressed flat against the wall of the lower valve chamber 6a, and on the other hand it also fills the lower bore section 13a of the valve push button 8, so that the shaft 8c is spread apart and the sealing lip 12 is pressed against the wall of the lower valve chamber 6a.

Depending on the desired aspiration capacity, the operator opens up an outwardly open aspiration regulating opening 17 of the aspirating channel 3 to different widths. The operator holds the flushing and aspirating device 1 in his or her hand and can use their thumb or index finger to operate the valve push button 8 and/or to cover the aspiration regulating opening 17 to different widths.

By pressing down on the actuating section 8a which projects from the device housing 2, the valve push button 8 can be moved from the valve starting position to the valve end position shown in FIG. 1b, in which the sealing lip 11 formed on the middle section 8b rests against a shoulder 19 of the valve chamber 6. In the valve end position, the sealing lip 12 formed on the bottom of the shaft 8c is moved beneath the flushing channel 4 which empties into the lower valve chamber 6a, so that the connection of the flushing channel 4 to the flushing and aspirating channel 5 is opened up by the annular chamber formed by the shaft 8c, which is set back radially inwardly, and the connection of the flushing and aspirating channel 5 to the aspirating channel 3 is either totally blocked by the sealing lip 11 formed on the middle section 8b, as shown in FIG. 1b, or throttled if the actuation is slight. In the exemplary embodiment shown, either flushing or aspirating can be done in the valve end positions.

After being released, the valve push button 8 is again forced by the reset spring 7 back to the valve starting position and in this way the connection between the flushing channel 4 and the flushing and aspirating channel 5 is again closed.

Due to the fact that the annular shoulder 14 against which the reset spring 7 is braced is situated in the wider middle region 8b, the shaft 8c is not deformed by the spring force of the reset spring 7 and thus the sealing action of the sealing lip 12 is not adversely affected. The diameter of the shaft is chosen such that the shaft wall has enough stability and does not present any obstacle during the aspiration.

In each position of the valve push button 8, the sealing lip 10 formed on the middle section 8b at the top seals off the middle section 8b against the upper valve chamber 6b, so that no secretion or flushing water can outwardly escape from the upper valve chamber 6b and get onto the hands of the operator.

Figure 3A:
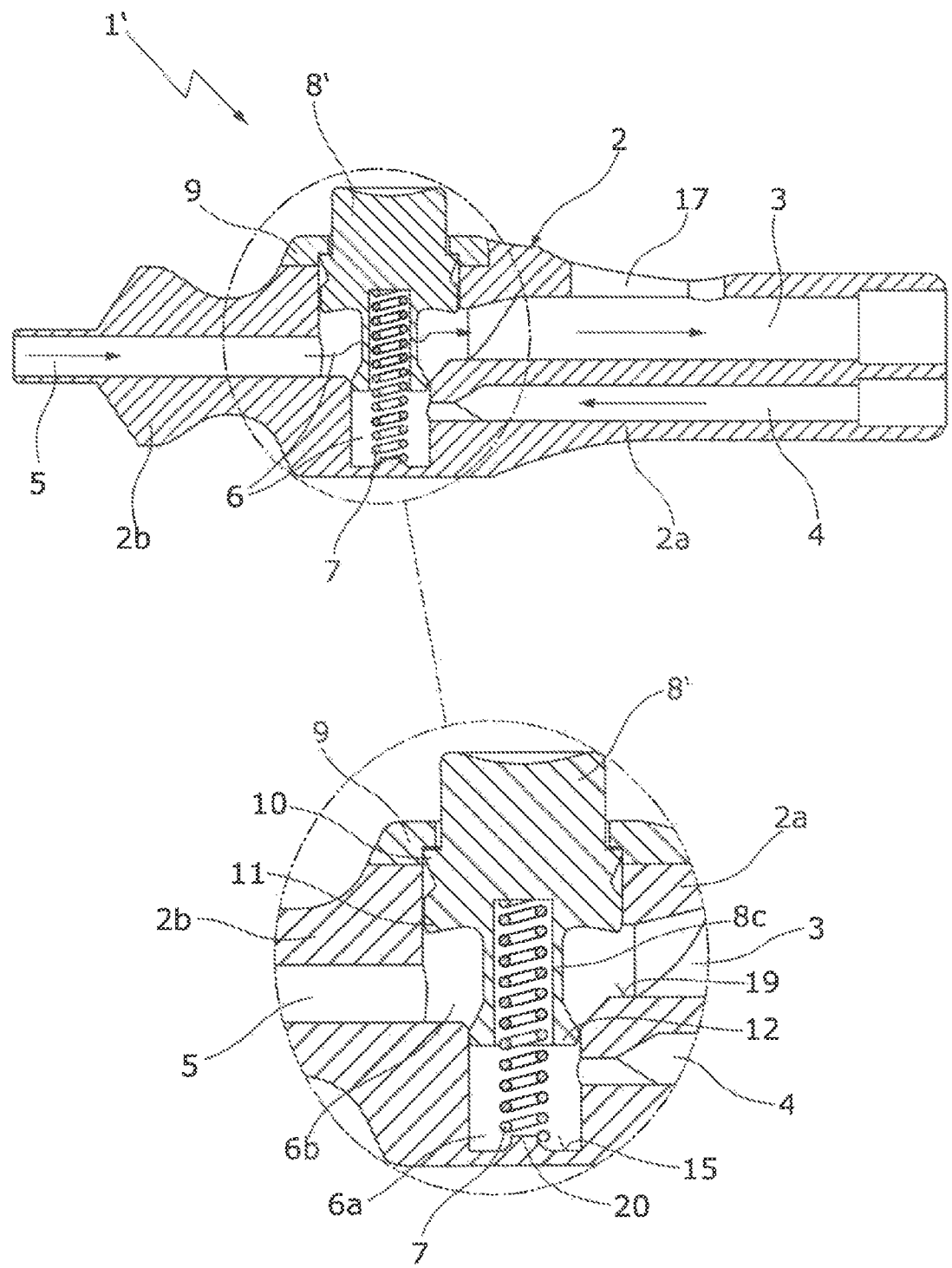
FIGS. 3a, 3b show a longitudinal section of a second embodiment of the flushing and aspirating device according to the invention with a valve push button, which is shown in FIG. 3a in a valve starting position and in FIG. 3b in a valve end position.
Figure 3B:
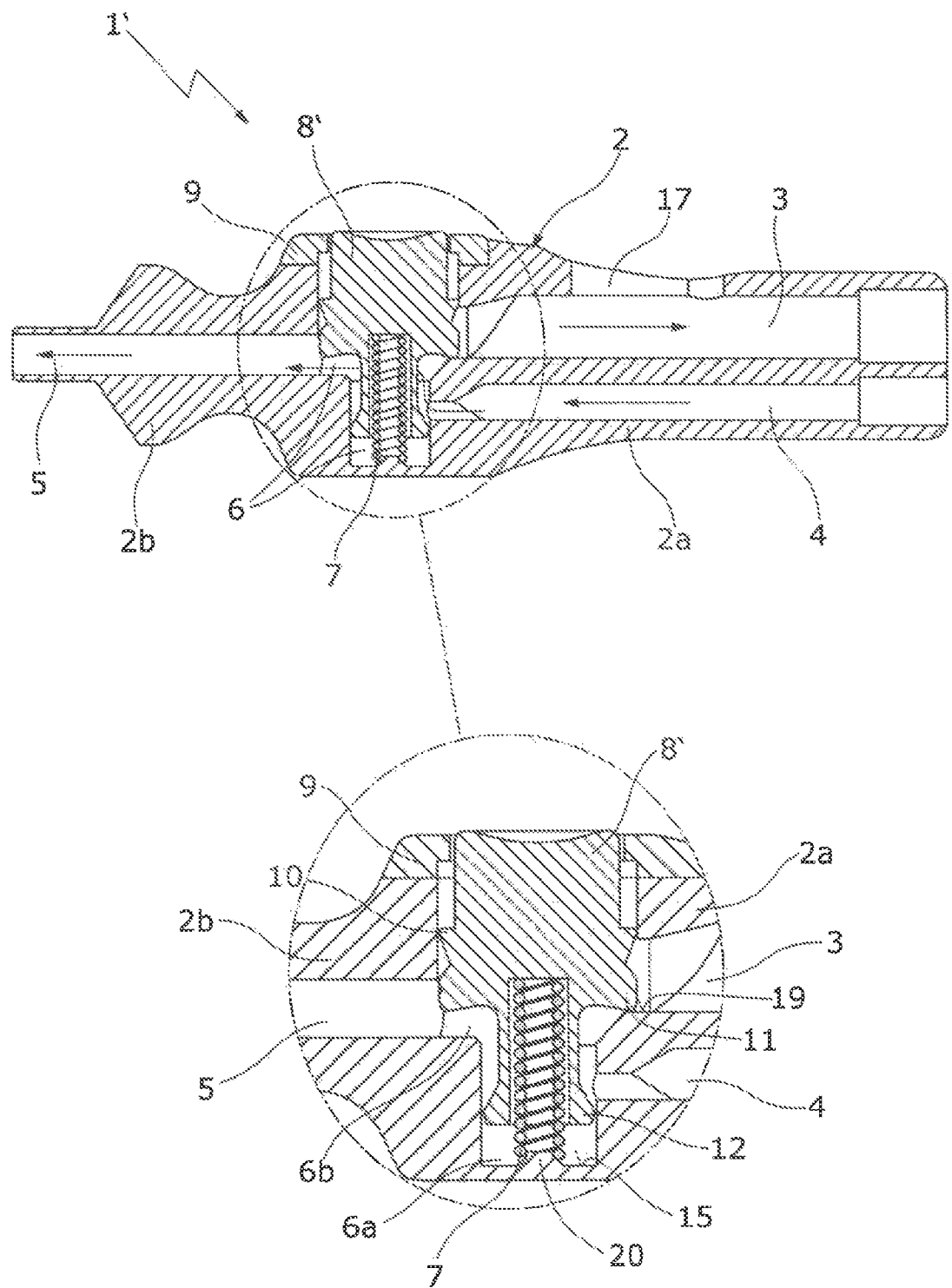
Figure 4A:
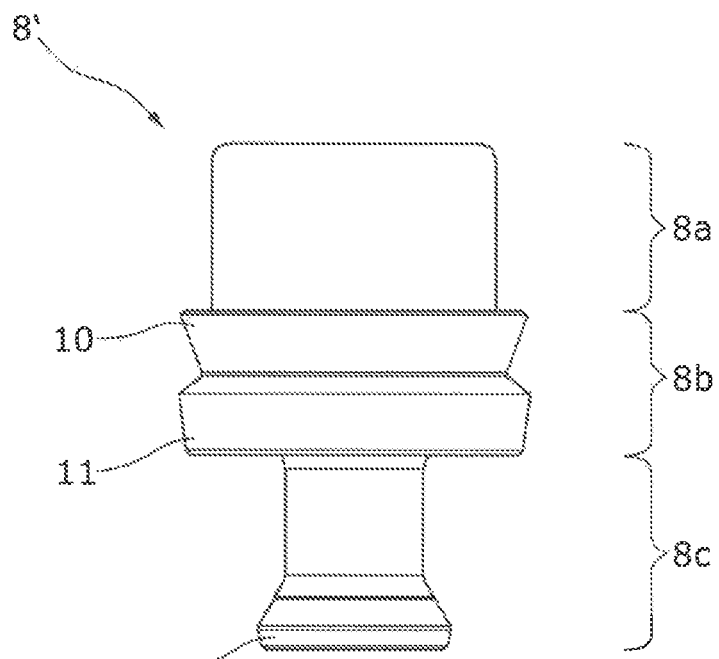
FIGS. 4a, 4b show a side view (FIG. 4a) and a cross sectional view (FIG. 4b) of the valve push button shown in FIGS. 3a, 3b.
Figure 4B:
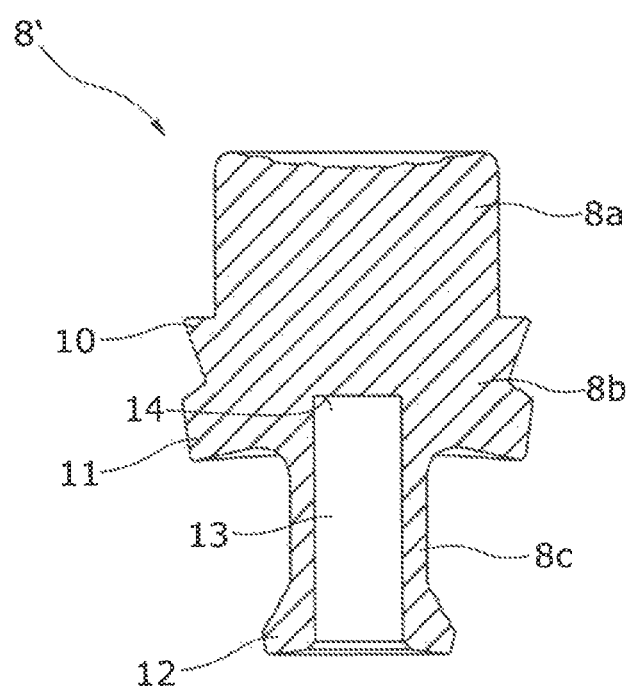

The flushing and aspirating device 1' shown in FIGS. 3a, 3b differs from the flushing and aspirating device 1 in that here no guiding projection for the valve push button 8' rises up from the housing bottom 15 and the valve push button 8' shown in FIGS. 4a, 4b has a bore 13 which is open towards the housing bottom 15 of the valve chamber 6, with a base of the bore 14 against which the reset spring 7 is braced. The other end of the reset spring 7 is secured in position against a small projection 20 of the housing bottom 15.

What is claimed is:

1. A flushing and aspirating device, comprising:
   a device housing comprising:
      an aspirating channel;
      a flushing channel;
      a flushing and aspirating channel; and
      a valve chamber in which the channels empty or emerge therefrom, respectively; and
   a manually operable valve push button which is movably guided in the valve chamber against the force of a reset spring and which has at least one sealing section for controlling the connection of the flushing and aspirating channel to the aspirating channel and/or the flushing channel;
   wherein the valve chamber is configured stepped, with a first valve chamber having a larger diameter, in which the aspirating channel and the flushing and aspirating channel empty or emerge therefrom, and with a second valve chamber having a smaller diameter, in which the flushing channel empties;
   wherein the valve push button comprises an actuating section, a shaft and a middle section in between, relative to which the shaft is set back radially inwards;
   wherein the middle section has at least one sealing section and the shaft has a sealing section, an outer diameter of the sealing section of the shaft being smaller than an outer diameter of the at least one sealing section of the middle section,
   wherein the at least one sealing section of the middle section is guided and sealed in the first valve chamber and the sealing section of the shaft is guided and sealed in the second valve chamber;
   wherein the valve push button including the sealing sections is formed as a single piece of an elastic rubber material;
   wherein the sealing section of the shaft is formed as a radially outwardly projecting annular sealing lip as being part of the single piece, which blocks the connection of the flushing and aspirating channel to the flushing channel in a first valve position of the valve push button and releases it in a second valve position of the valve push button; and
   wherein the at least one sealing section of the middle section is formed as a radially outwardly projecting annular sealing lip as being part of the single piece, which releases the connection of the flushing and aspirating channel to the aspirating channel in the first valve position of the valve push button and blocks it in the second valve position.

2. The flushing and aspirating device according to claim 1, wherein the valve push button comprises a bore, which is open towards a housing bottom of the valve chamber, with a shoulder being a base of the bore, against which the reset spring is braced.

3. The flushing and aspirating device according to claim 1, wherein a guiding projection rises up from a housing bottom of the valve chamber, on which both the valve push button and the reset spring are guided.

4. The flushing and aspirating device according to claim 3, wherein the valve push button comprises a stepped blind bore, which is open towards a housing bottom of the valve chamber, having a smaller and a larger bore diameter and having a shoulder, against which the reset spring is braced, the smaller bore diameter corresponding to the diameter of the guiding projection and the larger bore diameter corresponding at least to the outer diameter of the reset spring.

5. The flushing and aspirating device according to claim 4, wherein the shoulder is situated in a middle section or in an actuating section of the valve push button.

* * * * *